US00PP16684P2

(12) United States Plant Patent
Kanaya

(10) Patent No.: US PP16,684 P2
(45) Date of Patent: Jun. 20, 2006

(54) *CALIBRACHOA* PLANT NAMED 'SUNBELFIRE'

(50) Latin Name: ***Calibrachoa* sp.**
Varietal Denomination: Sunbelfire

(75) Inventor: Takeshi Kanaya, Shiga (JP)

(73) Assignee: Suntory Flowers Ltd., Tokyo (JP)

( * ) Notice: Subject to any disclaimer, the term of this patent is extended or adjusted under 35 U.S.C. 154(b) by 61 days.

(21) Appl. No.: 11/091,834

(22) Filed: Mar. 28, 2005

(51) Int. Cl.
*A01H 5/00* (2006.01)

(52) U.S. Cl. ..... Plt./263
(58) Field of Classification Search ..... Plt./356, Plt./263
See application file for complete search history.

(56) References Cited

U.S. PATENT DOCUMENTS

PP10,355 P * 4/1998 Murakami ..... Plt./356
PP14,605 P2 * 3/2004 Pierce ..... Plt./263

OTHER PUBLICATIONS

UPOV ROM GTITM Computer Databse, GTI Jouve Retrieval Software 2005/03 Citation for 'Sunbelfire'.*

* cited by examiner

*Primary Examiner*—Kent L. Bell
*Assistant Examiner*—W. C. Haas
(74) *Attorney, Agent, or Firm*—C. A. Whealy

(57) ABSTRACT

A new and distinct cultivar of *Calibrachoa* plant named 'Sunbelfire', characterized by its mounding and outwardly spreading plant habit; vigorous growth habit; freely branching habit; freely flowering habit; yellow and red bi-colored flowers; and good weather tolerance.

1 Drawing Sheet

Botanical designation: *Calibrachoa* sp.
Cultivar denomination: 'Sunbelfire'.

BACKGROUND OF THE INVENTION

The present Invention relates to a new and distinct cultivar of *Calibrachoa* plant, botanically known as *Calibrachoa* sp., and hereinafter referred to by the cultivar name 'Sunbelfire'.

The new *Calibrachoa* is a product of a planned breeding program conducted by the Inventor in Higashiomi, Shiga, Japan. The objective of the program is to create new *Calibrachoa* cultivars with uniform plant habit and attractive flower colors.

The new *Calibrachoa* originated as a single plant from a cross-pollination made by the Inventor in April, 2001 of proprietary seedling selection of *Calibrachoa* identified as code number R13, not patented, as the female, or seed, parent with a proprietary seedling selection of *Calibrachoa* identified as code number E20, not patented, as the male, or pollen, parent. The new *Calibrachoa* was discovered and selected by the Inventor in a controlled environment in Higashiomi, Shiga, Japan.

Asexual reproduction of the new cultivar by terminal cuttings in a controlled environment in Higashiomi, Shiga, Japan since September, 2003, has shown that the unique features of this new *Calibrachoa* are stable and reproduced true to type in successive generations.

SUMMARY OF THE INVENTION

Plants of the cultivar Sunbelfire have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Sunbelfire'. These characteristics in combination distinguish 'Sunbelfire' as a new and distinct cultivar of *Calibrachoa:*

1. Mounding and outwardly spreading plant habit.
2. Vigorous growth habit.
3. Freely branching habit.
4. Freely flowering habit.
5. Yellow and red bi-colored flowers.
6. Good weather tolerance; tolerant to rain and low and high temperatures.

Plants of the new *Calibrachoa* differ from plants of the female parent selection in plant height as plants of the new *Calibrachoa* are shorter than plants of the female parent selection. Plants of the new *Calibrachoa* differ from plants of the male parent selection in petal shape as plants of the male parent selection have petals with rounded apices. In addition, plants of the new *Calibrachoa* and the parent selections differ in petal coloration as plants of the parent selections have solid red-colored petals.

Plants of the new *Calibrachoa* can be compared to plants of the cultivar Sunbelchipi, disclosed in U.S. Plant Pat. No. 10,355. In side-by-side comparisons conducted in Higashiomi, Shiga, Japan, plants of the new *Calibrachoa* were more compact and had smaller leaves than plants of the cultivar Sunbelchipi. In addition, plants of the new *Calibrachoa* and the cultivar Sunbelchipi differed in petal coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa*.

The photograph at the top of the sheet comprises a side perspective view of a typical flowering plant of 'Sunbelfire' grown in a container.

The photograph at the bottom of the sheet is a close-up view of a typical flower and leaves of 'Sunbelfire'.

DETAILED BOTANICAL DESCRIPTION

In the following description, color references are made to The Royal Horticultural Society Colour Chart, 2001 Edition, except where general terms of ordinary dictionary significance are used. Plants grown in 15-cm containers for about four months were used for the aforementioned photographs and following description. Plants were grown under conditions which closely approximate commercial production conditions during the spring and early summer in Higashiomi, Shiga, Japan in an outdoor nursery. During the production period, day temperatures were about 22° C. and night temperatures were about 12° C. Plants were pinched one time.

Botanical classification: *Calibrachoa* sp. cultivar Sunbelfire.

Parentage:

*Female, or seed, parent.*—Proprietary seedling selection of *Calibrachoa* sp. identified as code number R13, not patented.

*Male, or pollen, parent.*—Proprietary seedling selection of *Calibrachoa* sp. identified as code number E20, not patented.

Propagation:

*Type cutting.*—Terminal vegetative cuttings.

*Time to initiate roots.*—About one week at 20° C. to 25° C.

*Time to produce a your rooted plant.*—About three weeks at 20° C. to 25° C.

*Root description.*—Fine, fibrous; light brown in color.

*Rooting habit.*—Freely branching.

Plant description:

*Plant form and growth habit.*—Annual flowering plant; initially upright to semi-upright, outwardly spreading to eventually cascading; uniformly mounded appearance. Vigorous growth habit.

*Plant height* (*from soil level to top of plant plane*).—About 14.5 cm.

*Plant diameter.*—About 53.8 cm.

*Branching habit.*—Freely branching, lateral branches potentially developing at every node; pinching enhances lateral branch development.

*Lateral branch description.*—Length: About 21.2 cm. Diameter: About 2 mm. Internode length: About 1 cm. Texture: Pubescent. Color: 144B.

*Foliage description.*—Arrangement: Alternate; simple; sessile. Length: About 4.3 cm. Width: About 1.3 cm. Shape: Lanceolate. Apex: Obtuse. Base: Cuneate. Margin: Entire. Texture, upper and lower surfaces: Pubescent. Venation pattern: Pinnate; arcuate. Color: Developing and fully expanded foliage, upper surface: 137A; venation, similar to lamina. Developing and fully expanded foliage, lower surface: 137C; venation, similar to lamina.

Flower description:

*Flower type and habit.*—Flowers face upright or outward; single, axillary; salverform. Flowers are persistent. Freely flowering habit, numerous flowers per plant. Flowers not fragrant.

*Natural flowering season.*—Spring to late autumn in Japan; flowering continuous during this period.

*Time to flower.*—Early flowering; plants begin flowering about three to four weeks after planting.

*Flower longevity on the plant.*—About seven to ten days.

*Flower size.*—Diameter: About 3.1 cm. Depth: About 1.9 cm.

*Flower buds.*—Length: About 1.9 cm. Diameter: About 4.4 mm. Shape: Elongated oblong. Color: 162C.

*Corolla.*—Arrangement/appearance: Single whorl of five petals, fused into flared trumpet. Petal length from throat: About 1.1 cm. Petal width: About 1.4 cm. Petal shape: Roughly fan-shaped. Petal apex: Acute. Petal margin: Entire. Petal texture, upper and lower surfaces: Smooth, glabrous; satiny. Throat texture: Smooth. Tube texture: Pubescent. Color: Petal, when opening and fully opened, upper surface: Ground color, 9A; longitudinal streaks, 42A. Petal, when opening and fully opened, lower surface: 37B. Flower throat (inside): 13A; venation, N199A. Flower tube (outside): 9C; venation, N199A.

*Sepals.*—Arrangement/appearance: Single whorl of five sepals, fused at base; star-shaped. Length: About 1.3 cm. Width: About 3 mm. Shape: Lanceolate. Apex: Acute. Margin: Entire. Texture, upper and lower surfaces: Pubescent. Color, upper and lower surfaces: 137A.

*Peduncles.*—Length: About 3.2 cm. Width: About 0.4 mm. Strength: Moderately strong. Angle: Erect to about 45° from vertical. Texture: Pubescent. Color: 144A.

*Reproductive organs.*—Stamens: Quantity: Five per flower. Anther shape: Ellipsoidal. Anther length: Less than 1 mm. Anther color: 5B. Pollen amount: Moderate. Pollen color: 8A. Pistils: Quantity: One per flower. Pistil length: About 9 mm. Stigma shape: Elliptic. Stigma color: 143C. Style length: About 8.5 mm. Style color: 144D. Ovary color: 144B.

*Seed/fruit.*—Seed and fruit production has not been observed.

Disease/pest resistance: Plants of the new *Calibrachoa* have not been noted to be resistant to pathogens and pests common to *Calibrachoas*.

Weather/temperature tolerance: Plants of the new *Calibrachoa* are tolerant to rain and wind and have been observed to tolerate temperatures from 5° C. to 35° C.

It is claimed:

1. A new and distinct cultivar of *Calibrachoa* plant named 'Sunbelfire', as illustrated and described.

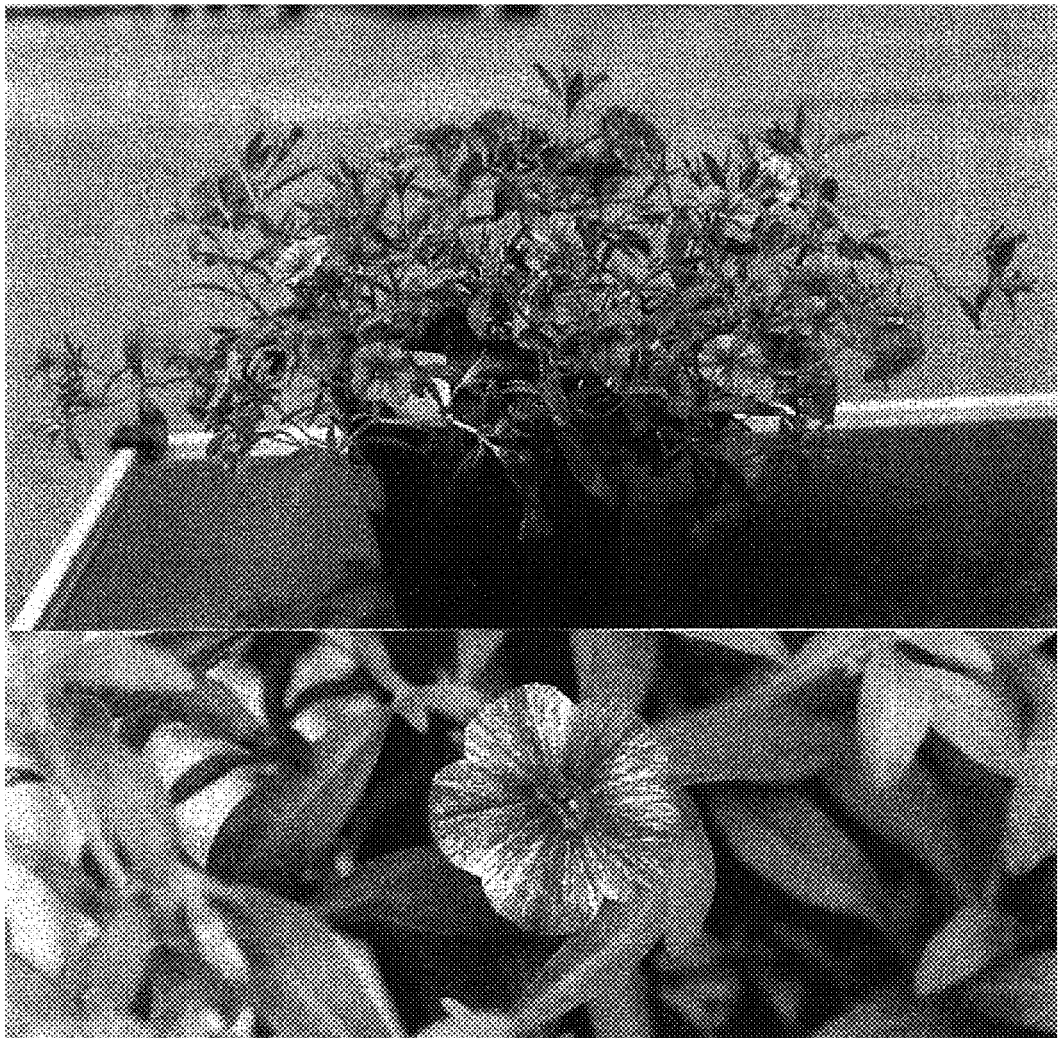

* * * * *